United States Patent
Kwok

(10) Patent No.: US 9,144,654 B2
(45) Date of Patent: Sep. 29, 2015

(54) SNORING TREATMENT APPARATUS AND METHODS OF MANAGING SNORERS

(75) Inventor: Philip Rodney Kwok, Bella Vista (AU)

(73) Assignee: RESMED LIMITED, Bella Vista (AU)

( * ) Notice: Subject to any disclaimer, the term of this patent is extended or adjusted under 35 U.S.C. 154(b) by 1990 days.

(21) Appl. No.: 11/578,301

(22) PCT Filed: Apr. 15, 2005

(86) PCT No.: PCT/AU2005/000538
§ 371 (c)(1),
(2), (4) Date: Apr. 13, 2007

(87) PCT Pub. No.: WO2005/099798
PCT Pub. Date: Oct. 27, 2005

(65) Prior Publication Data
US 2007/0215156 A1  Sep. 20, 2007

(30) Foreign Application Priority Data
Apr. 15, 2004 (AU) ................................ 2004902019

(51) Int. Cl.
*A61M 16/00* (2006.01)
*A61M 16/06* (2006.01)
(Continued)

(52) U.S. Cl.
CPC ................... *A61M 16/06* (2013.01); *A61F 5/56* (2013.01); *A61M 16/0051* (2013.01); *A61M 16/0069* (2014.02); *A61M 16/107* (2014.02); *A61M 11/00* (2013.01); *A61M 16/0666* (2013.01); *A61M 16/0683* (2013.01); *A61M 16/1055* (2013.01); *A61M 16/208* (2013.01); *A61M 2016/0021* (2013.01); *A61M 2016/0024* (2013.01); *A61M 2021/0016* (2013.01); *A61M 2205/18* (2013.01); *A61M 2205/3375* (2013.01);
(Continued)

(58) Field of Classification Search
CPC ..... A61M 16/00; A61M 16/06; A61M 16/10; A61M 16/1005; A62B 9/00; A62B 9/006; A62B 18/02; A62B 18/08
USPC ............. 128/204.18, 204.21, 204.23, 204.26, 128/205.25
See application file for complete search history.

(56) References Cited

U.S. PATENT DOCUMENTS 4,461,293 A * 7/1984 Chen ......................... 128/204.23
6,349,724 B1 * 2/2002 Burton et al. ............ 128/204.18
(Continued)

FOREIGN PATENT DOCUMENTS

CN       1440302 A    9/2003
WO    WO 88/10108    12/1988
(Continued)

OTHER PUBLICATIONS

Office Action and English Translation for corresponding Chinese Application No. 200580011477.9, issued Apr. 3, 2009, 18 pages.
(Continued)

*Primary Examiner* — Valerie L Skorupa
(74) *Attorney, Agent, or Firm* — Nixon & Vanderhye, P.C.

(57) ABSTRACT

Method and apparatus are provided for the treatment of a user's sleeping disorder, e.g., snoring. Positive pressure gas in the range of 8 cm $H_2O$ or less, preferably about 3-6 cm $H_2O$, is provided to the user's airways. If the pressure is greater than 6 cm $H_2O$, or between 6-8 cm $H_2O$, an indication or alert is provided to treat or diagnose the user with obstructive sleep apnea (OSA).

53 Claims, 6 Drawing Sheets

(51) Int. Cl.
*A61F 5/56* (2006.01)
*A61M 11/00* (2006.01)
*A61M 16/10* (2006.01)
*A61M 16/20* (2006.01)
*A61M 21/00* (2006.01)

(52) U.S. Cl.
CPC ....... *A61M 2205/36* (2013.01); *A61M 2205/52* (2013.01); *A61M 2205/581* (2013.01); *A61M 2205/587* (2013.01); *A61M 2230/50* (2013.01)

(56) References Cited

U.S. PATENT DOCUMENTS

| | | | |
|---|---|---|---|
| 6,435,184 | B1* | 8/2002 | Ho .......................... 128/206.21 |
| 6,705,315 | B2 | 3/2004 | Sullivan et al. |
| 2001/0027791 | A1* | 10/2001 | Wallace et al. .......... 128/204.21 |
| 2002/0007127 | A1* | 1/2002 | Sullivan et al. ............... 600/529 |
| 2002/0023649 | A1* | 2/2002 | Gunaratnam et al. ... 128/205.25 |
| 2002/0083122 | A1* | 6/2002 | Lemchen ...................... 709/203 |
| 2003/0066529 | A1* | 4/2003 | Truschel et al. ......... 128/204.18 |
| 2003/0172930 | A1 | 9/2003 | Kullik et al. |
| 2004/0163648 | A1* | 8/2004 | Burton ..................... 128/204.21 |
| 2005/0005935 | A1* | 1/2005 | Gradon ................... 128/204.18 |
| 2005/0098179 | A1* | 5/2005 | Burton et al. ............ 128/205.24 |
| 2011/0061647 | A1* | 3/2011 | Stahmann et al. ....... 128/202.16 |

FOREIGN PATENT DOCUMENTS

| | | |
|---|---|---|
| WO | WO 96/40335 | 12/1996 |
| WO | 02/02169 A1 | 1/2002 |
| WO | 02/18002 A1 | 3/2002 |
| WO | WO 02053217 A1 * | 7/2002 |
| WO | 03/024335 A1 | 3/2003 |
| WO | WO 03/030804 | 4/2003 |

OTHER PUBLICATIONS

International Search Report for PCT/AU2005/000538 dated May 31, 2005.

Supplementary Partial European Search Report for co-pending European Application No. 05729484, mailed Sep. 29, 2009, 5 pages.

Examiner's Report No. 2 for corresponding Australian Appln. 2005232336, mailed Apr. 29, 2011, 2 pages.

Australian Agent's Response for corresponding Australian Appln. 2005232336, mailed Jul. 28, 2011, 3 pages.

Examiner's Report No. 3 for corresponding Australian Appln. 2005232336, mailed Sep. 8, 2011, 2 pages.

Australian Agent's Response for corresponding Australian Appln. 2005232336, mailed Nov. 14, 2011, 2 pages.

Examiner's Report No. 4 for corresponding Australian Appln. 2005232336, mailed Nov. 22, 2011, 4 pages.

Australian Agent's Response for corresponding Australian Appln. 2005232336, mailed Dec. 8, 2011, 2 pages.

AU Application Details for corresponding Australian Appln. 2005232336 indicating Application Status: Accepted http://pericles.ipaustralia.gov.au/ols/auspat/applicationDetails.do, printed Dec. 14, 2011.

* cited by examiner

SNORING TREATMENT APPARATUS AND METHODS OF MANAGING SNORERS

CROSS REFERENCE TO RELATED APPLICATION

This application is the US national phase of international application PCT/AU2005/000538 filed 15 Apr. 2005, which designated the U.S. and claimed priority of AU 2004902019 filed 15 Apr. 2004, the entire contents of each of which are hereby incorporated by reference.

FIELD OF THE INVENTION

The present invention relates to apparatus and methods for the treatment of snoring, and for the management of snoring with a view to improving the early diagnosis and treatment of obstructive sleep apnea (hereinafter referred to as 'OSA').

BACKGROUND

Snoring (and other sleep disordered breathing) have major consequences to the community, both social and medical. Some studies suggest that more than a third of adults report that they snore at least a few nights a week. It is possible that about 40% of middle-aged men snore versus about 30% of middle-aged women. It has been reported that 30% of those over the age of 30 are snorers.

Snoring may be controlled with modification to several factors including obesity, smoking, alcohol consumption and late night eating. These are however behavioural and therefore most of the population have difficulty in modifying these.

SUMMARY OF THE INVENTION

An aspect of this invention is to overcome one or more of the existing social and medical problems associated with snoring. Preferably, the invention will also serve to identify patients at earlier stages in life, and indicate to a patient when the social problem of snoring may be developing into the medical one such as OSA. Use of the invention will also encourage improved long-term compliance if the patient develops medical conditions like OSA later in life.

According to one embodiment of the present invention, there is provided a system for treatment of a user with a sleeping disorder, comprising a flow generator to generate a flow of gas that is pressurized up to a maximum of about 8 cm $H_2O$, and a user interface coupled to the flow generator and structured to deliver the pressurized gas to the user's airways in use.

In another embodiment of the present invention, there is provided a method of predicting the possible onset of obstructive sleep apnea (OSA), comprising monitoring a snore parameter of a user; and applying gas under positive pressure to the user's airways in dependence on the monitored snore parameter.

In yet another embodiment of the invention, there is provided a method of treating snoring, comprising applying positive airway pressure to the snorer's airways in use up to a range of about 8 cm $H_2O$ or less during an entire respiratory cycle of the snorer, for all treatment sessions of the snorer.

In still another embodiment of the invention, there is provided a system for treatment of a user with a progressively worsening sleeping disorder, comprising a snore treatment unit configured for treatment of snoring of the user; an OSA/snore treatment unit configured for treatment of OSA and snoring of the user; and an upgradable base unit configured to alternatively cooperate with the snore treatment unit and the OSA/snore treatment unit.

According to a further embodiment of the invention, there is provided a method for treating snoring, comprising applying a minimum pressure to the airways of the snorer, monitoring a snoring parameter of the snorer, and comparing the snoring parameter to a predetermined amount, wherein if the snore parameter is greater than said predetermined amount, increasing the minimum pressure by an incremental amount, and if the snore parameter is less than said predetermined amount, maintaining at least the minimum pressure.

Still another embodiment of the invention relates to a system of managing a snorer comprising means for applying positive airway pressure; means for determining according to predetermined criteria the likely onset of OSA; and means for producing an alert as to the possible need for diagnosis or treatment of OSA.

A further embodiment of the present invention relates to a method for acclimatizing a user for treatment of obstructive sleep apnea, comprising providing the user with a patient interface; and applying gas to the patient interface in a pressure range sufficient for treatment of snoring but less than sufficient for treatment for OSA.

In another aspect the invention resides in a method of managing a snorer including the steps of treating snoring by means of positive airway pressure apparatus during a period in the life of the snorer when the snorer does not suffer from OSA, the treatment including determining according to predetermined criteria the likely onset of OSA and alerting the snorer to the possible need for diagnosis or treatment of OSA.

Preferably such a method includes the further step of substituting continuous positive air pressure treatment (herein after referred to as 'CPAP') for anti-snoring treatment at the onset of OSA.

The method can include the step of providing an alerting apparatus whereby the snorer or associated person is alerted to onset of OSA.

The associated person can be a bed partner, a spouse, person sleeping in another room, or any other person, who may be alerted.

An embodiment of the invention also resides in patient apparatus for the treatment of snoring by the administration of positive airway pressure including a snoring behaviour monitor, a comparator for comparing snoring behaviour of the patient during a period of the life of the patient with snoring behaviour during a subsequent period of the life of the patient and determining according to predetermined criteria the likely onset of OSA and alerting the patient, bed partner, spouse or other associated person, to this.

These and other aspects will be described in or be apparent from the following detailed description of preferred embodiments.

BRIEF DESCRIPTION OF FIGURES

Embodiments of the present invention will now be described by way of example only, with reference to the accompanying Figures, in which.

DETAILED DESCRIPTION OF PREFERRED EMBODIMENTS

Figure 1:
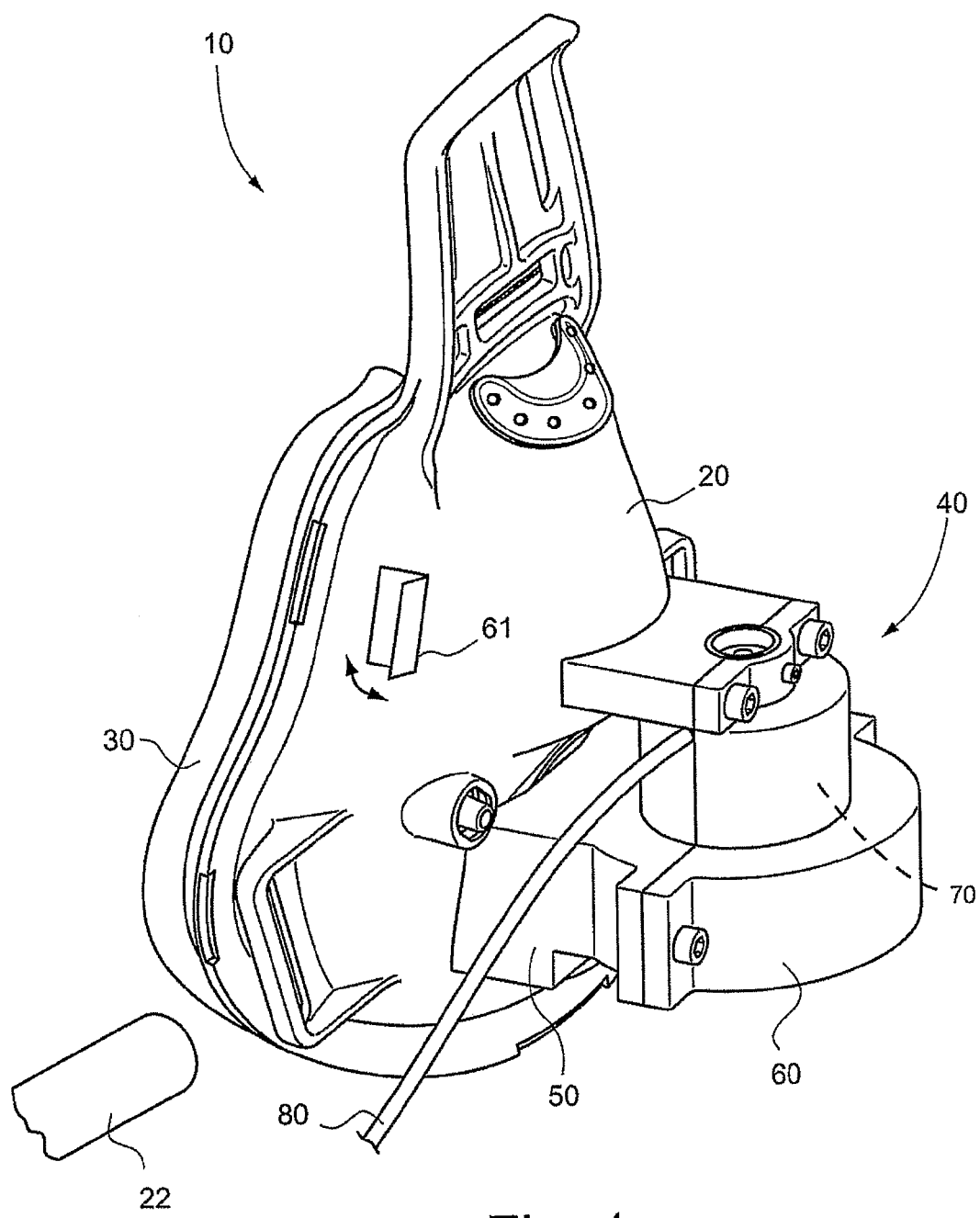
FIG. 1 is a perspective view of a treatment system according to an embodiment of the present invention.

Embodiments of the present invention will be described in the following text. In a preferred form, the apparatus of the invention includes an integrated flow generator and mask system. Such a system is described in our co-pending patent application Nos. U.S. 60/505,718, filed Sep. 25, 2003, and PCT/AU04/01309, filed Sep. 27, 2004, each entitled "VENTILATOR MASK AND SYSTEM" and incorporated by reference in its entirety. An exemplary drawing is shown in FIG. 1 herein. The mask system 10 includes a full face mask having a frame 20 and a face contacting portion in the form of a cushion 30. System 10 includes a flow generator 40 having housing portions 50 and 60 which support a motor 70 which is supplied with power, e.g., via cord 80. Further details of this system are included in the above mentioned co-owned patent applications.

While the system shown in FIG. 1 is preferred, for reasons that will become apparent, other more conventional arrangements are within the spirit and scope of the present invention. For example, any user interface that is capable of delivering pressurized gas to a user's airways may be substituted for the fall face mask shown in FIG. 1. User interfaces may include nasal masks, oral masks, nasal cannulae, oro-nasal masks, prongs, nozzles, etc. Further, conventional flow generators may be employed as well, such as those which are not built into the patient interface. Whatever system components are used, they are designed to be as unobtrusive to the user as possible, with low noise generation, ease of use, an appearance of being user friendly and small size.

Apply Pressure to Treat Snoring

The flow generator may be configured to provide an adjustable or constant supply of pressurized gas to the user's airways, via the patient interface. The pressure supplied by the flow generator is sufficient to reduce or prevent snoring without being in the higher range of pressure normally required for the treatment of OSA. Generally, the flow generator will be capable of supplying a pressure of up to about 8 cm $H_2O$ maximum, although treatment of snoring only usually occurs at pressures of less than 6 cm $H_2O$. The average pressure range during a snore treatment session will be about 3-6 cm $H_2O$. Stated differently, an aspect of the invention is directed to a flow generator that is designed for snoring treatment but not for treatment of OSA. Such a system is beneficial since it can acclimatize the user for OSA treatment in the event the snoring progresses to OSA.

Although pressure up to approximately 8 cm $H_2O$ can be required to prevent snoring, such pressures may be more indicative of the presence of OSA, where prescribed CPAP equipment (typical pressures of 4 cm $H_2O$ to 20 cm $H_2O$ with an average of 10 cm $H_2O$ to 12 cm $H_2O$) will be more suitable.

Monitor Snoring Parameter

Figure 2:
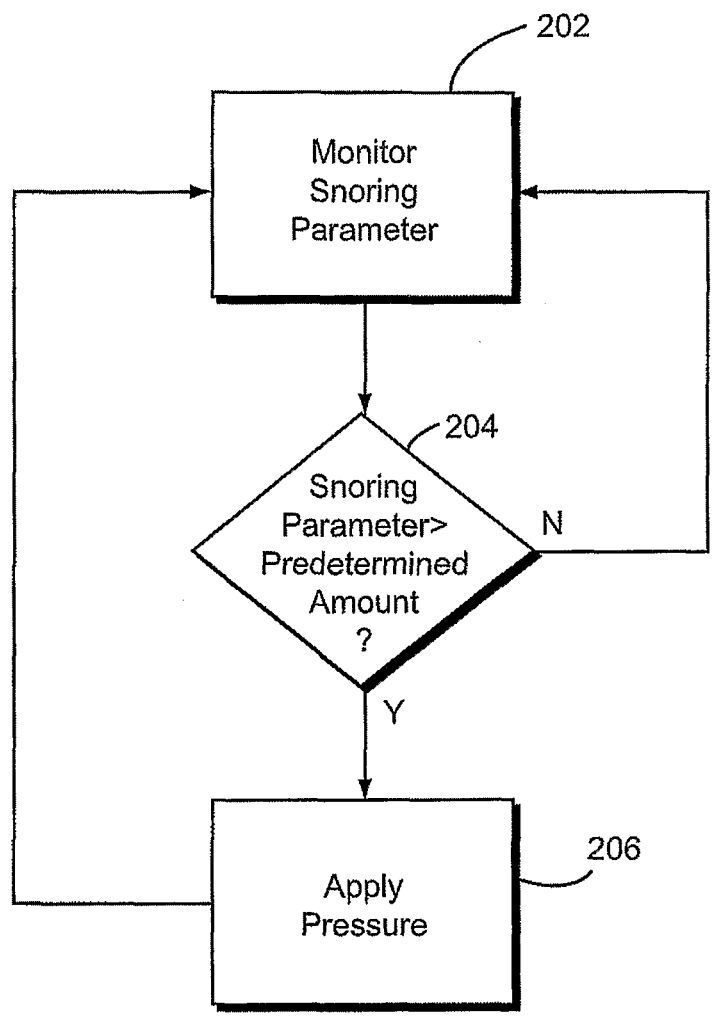
FIG. 2 is a block diagram according to an embodiment of the present invention.

In a more advanced embodiment, one or more components of the system in FIG. 1 is configured to monitor a snoring parameter of the user. This step is represented by box 202 in FIG. 2. The snoring parameter may include multiple parameters, all of which parameters are known in the art. For example, the system can use automatic setting of the operating pressure in response to the detection of snoring by such means as a pressure sensor with appropriate filters to distinguish the pressure fluctuations characteristic of snoring, or by other means such as a microphone with appropriate filtering. Where a microphone is used, it should be placed or controlled in such a way to prevent influence from a snoring bed partner.

In box 204, a determination is made as to whether the monitored snoring parameter is greater than a predetermined amount, e.g., is the detected sound or pressure greater than a predetermined sound level or pressure? If the snoring parameter is greater than a predetermined amount, pressure is supplied to the user's airways, as indicated in box 206. If the monitored parameter is not greater than the predetermined amount, the snoring parameter is again monitored in box 202. The pressure may be reduced or eliminated if the snoring parameter is less than the predetermined amount.

Figure 3:
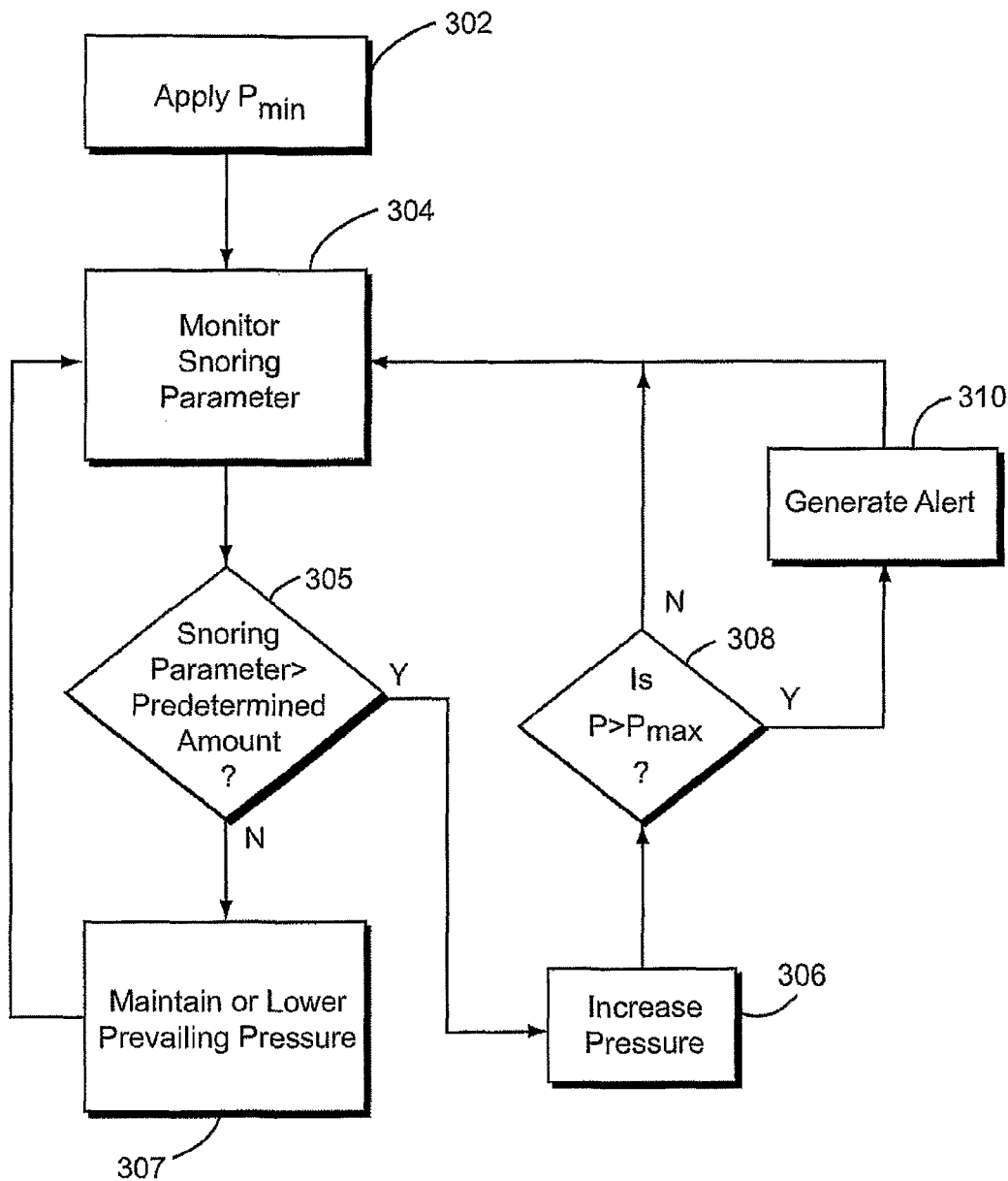
FIG. 3 is a block diagram according to an embodiment of the present invention.

A slight variation of this embodiment is shown in FIG. 3, in which a minimum pressure is initially supplied to the user, per box 302. In box 304, a snoring parameter of the patient is monitored. If a determination is made in box 305 that the monitored parameter is greater than a predetermined amount, the prevailing pressure, e.g., the minimum pressure, is increased, per box 306. If the monitored parameter is lower than the predetermined amount, the minimum or then prevailing pressure is maintained, per box 307.

Thus, the system is initially set to operate in a minimum pressure mode until the detection of snoring, and then gradually increases the operating pressure, either in stages (incrementally or step-wise) or continuously, until snoring stops. For example, an autoset system with airflow limitation technology can be utilized. Alternatively, the device can simply be capable of running at a pre-selected pressure, which the user chooses by experimentation.

Provide an Alert or Indication

Figure 4:
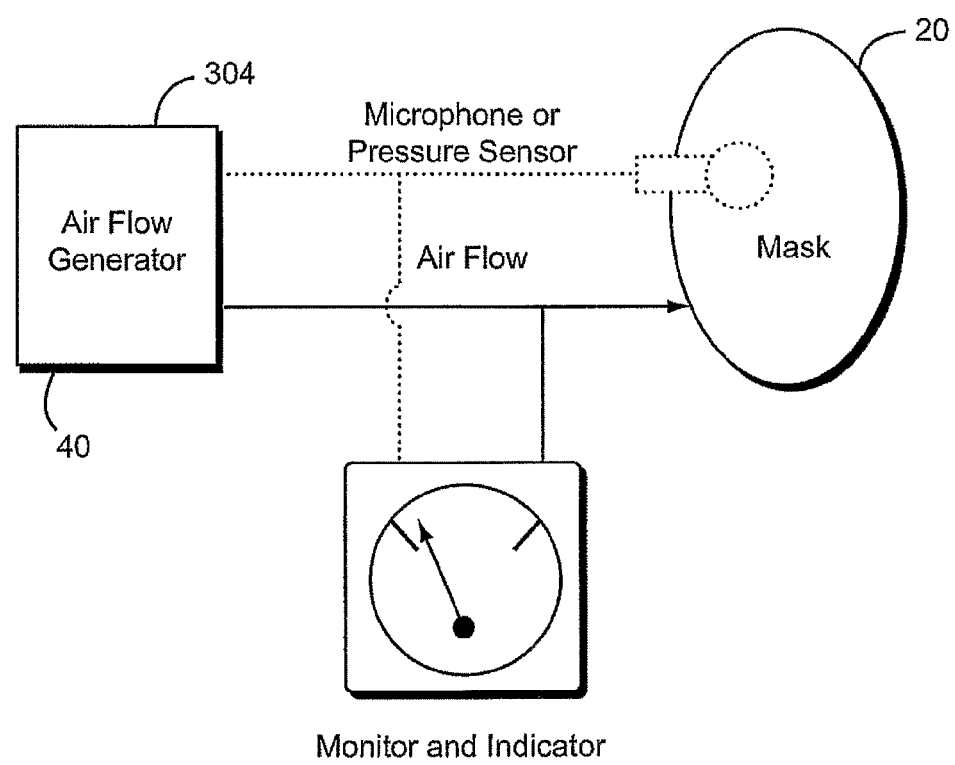
FIG. 4 is a schematic block diagram of components of a user apparatus according to an embodiment of the present invention.

Still referring to FIG. 3, the next step is to determine whether the prevailing pressure is greater than a predetermined amount, per box 308. If the prevailing pressure is greater than the maximum pressure for treatment of snoring only, e.g., about 6 cm $H_2O$, an alert or indicator is generated per box 310. For example, an alerting device can be a lamp or other visual indicator, an audible signal or the like. FIG. 4 schematically represents a visual indicator such as a gauge and needle. The indicator may be a message provided with a product manual. The alert or indicator may be provided without the intervention of a clinician.

Manual Setting of Operating pressure

The operating pressure can be set manually by the user, or can be adjusted automatically by the unit, in response to monitoring of the user. Where manual control is employed, the device can be manually adjusted (e.g., via a remote control) by a user or bed partner according to the severity of snoring or be set in response to snoring so that a setting is found that is low enough to control the snoring. Once the maximum pressure for the device is reached, this can signify to the patient that a sleep physician should be consulted. It could be suspected that OSA would be present should a pressure of about 6 cm $H_2O$ to 8 cm $H_2O$ is required to control snoring.

Should the device not be used at the optimum pressure setting due, for example, to patient discomfort, the patient or bed partner can still choose to operate the equipment at a lower pressure setting, and although snoring may still occur, it may be at reduced severity or intensity. Benefits can thus still be gained by both the user and the user's sleeping partner with reduced compliance issues for the user.

Monitor Breathing Cycle

Figure 5:
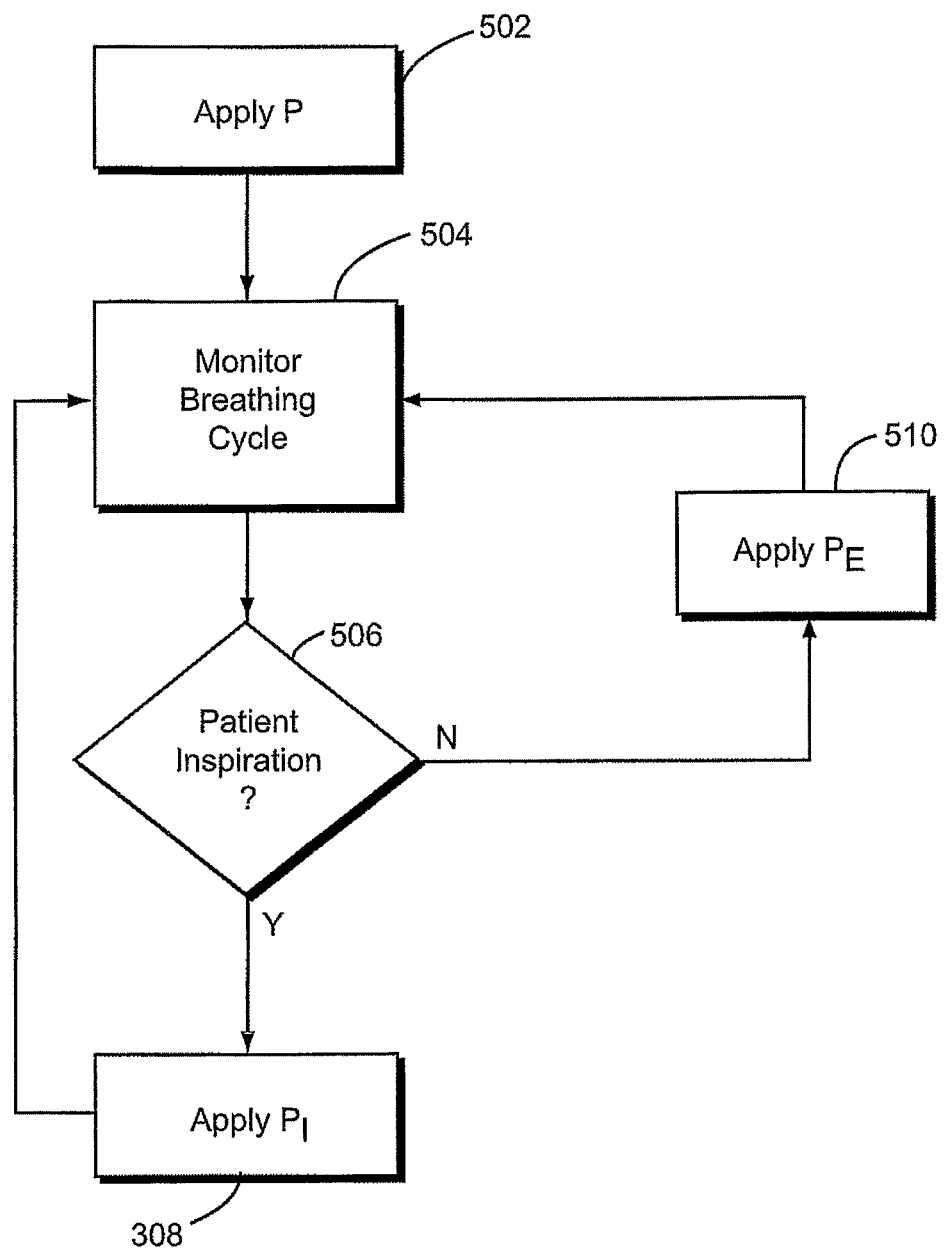
FIG. 5 is a block diagram according to an embodiment of the present invention.

The system can also include a bi-level flow generator, or any other variable pressure device delivering a flow of gas, in synchrony with a breathing patient, to improve breathing comfort. For example, as shown in FIG. 5, a nominal pressure may be applied to the user, per box 502. In box 504, the user's breathing cycle is monitored, e.g., to determine when the patient is in the inspiration or expiration stage of the user's breathing cycle. Also, the transition between inspiration and expiration can be monitored, e.g., by conventional well known means. If the user is determined in box 506 to be in the inspiration mode, then inspiration pressure $P_I$ is supplied to the user, per box 508. If the user is not in the inspiration stage, then expiration pressure ($P_E$) is applied to the user, per box 510. $P_I$ is generally greater than $P_E$. For example, $P_I$ may be in the range of 3-6 cm $H_2O$ to treat snoring, while $P_E$ is less, e.g., 2-5 cm $H_2O$ or less, or even nil or negligible.

The flow generator may drop to zero pressure on or immediately prior to exhalation, thus reducing exhalation effort. This may be achieved by switching off the blower, or opening a blow off valve, during exhalation. Alternatively or additionally, in another form the device can deliver a pulse of air during inhalation and somewhere between zero breathing air flow and a relatively low volume of breathing air flow or an adequate flow for $CO_2$ washout, the device can reduce pressure swing to reduce the work of breathing out, which is the active component of breathing.

Criteria for alerting need to diagnose or treat user for OSA

Criteria which can be employed, either alone or in combination, for alerting a user to the possible need for diagnosis or treatment of OSA include:

(a) the consistent need for relatively high pressure to prevent snoring such as 6 cm $H_2O$ to 8 cm $H_2O$;

(b) the monitoring of snoring and breathing waveform (i.e. the inhalation and exhalation cycle) to detect the absence of breathing after the cessation of snoring. For example, if the device 'hears' nothing after a session of snoring and no breathing waveform (inhalation/exhalation cycle) are not recognised, the indicator prompts the user;

(c) the detection of apneas. For example, the device could signal when more than five significant closed apneas occur in the hour; and (d) monitoring of the progress of snoring severity over time (days, months or years). For example, if the device detects snoring progressively getting worse (louder and/or more severe) to the point where the unit trends towards the highest pressure setting, this may be pre-warning that progression to OSA is likely.

The system may include a memory that records the occurrence of such events. Other techniques for arriving at the user alert can be used in the practice of the invention.

Other optional features/techniques

Other features which can optionally be incorporated in the apparatus of the invention include the following.

In an embodiment pressure can be delivered only on inhalation where most snoring occurs, and pressure delivered to the user during exhalation may be negligible or nil.

The apparatus can modify pressure requirements to an upper limit or can be set by a snore rating by a user. The pressure control can be calibrated with indications of snorer intensity, with for example, heavy snorers selecting the highest setting.

The mask or interface can include a valve or valves 61 (FIG. 1), open during exhalation and closed during inhalation, that reduce exhalation effort to decrease work and improve comfort of breathing. Each valve (e.g., a flap) may open upon sufficient pressure produced during exhalation.

The mask or interface can include a passive or actively heated humidifier to improve breathing comfort.

The device can also be used as a clean air device with dust or bacterial filters.

Another version can incorporate filtration systems for allergy or asthma sufferers to minimise irritation during sleep.

Figure 6:
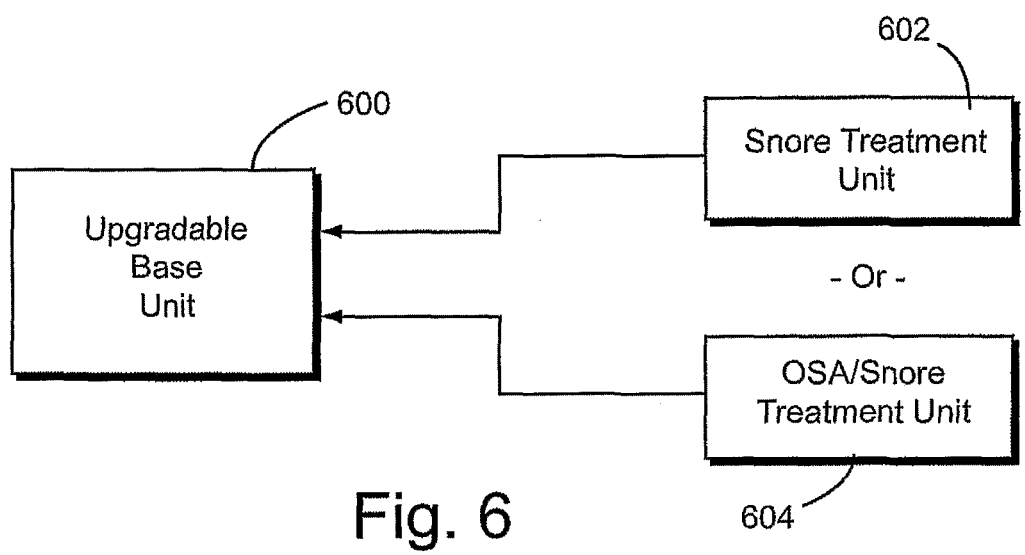
FIG. 6 is a schematic view of an upgradable system according to an embodiment of the present invention.

The device can be manufactured in a form which enables it to be upgraded to a CPAP system if and when a patient progresses from simply snoring to OSA. This can be achieved in a modular fashion, for example by providing a higher performance motor assembly and/or circuit board as a "plug-in" unit. For example, FIG. 6 shows in schematic fashion an upgradable base unit 600, a snore treatment unit 602 and an OSA/snore treatment unit 604. Upgradable base unit 600 may include a mask as shown in FIG. 1 that is configured to easily cooperate with a snore unit 602 in the form of a built-in motor integrated with the mask frame. Due to its size, the built-in flow generator is ideal for treatment of snoring only, since the motor 70 is generally smaller than motors supplied with conventional stand alone flow generators, but is still capable of generating pressure up to 8 cm $H_2O$. Further, the snore unit can be removed from the mask (upgradable base) such that it can cooperate with a larger capacity built-in motor unit, or with a stand alone flow generator, e.g., via an air delivery conduit. Of course, the base unit could be a flow generator capable of operating in snore treatment mode, e.g., 8 cm $H_2O$ or less, or OSA/snore treatment mode, e.g., 4-20 cm $H_2O$. Typically, treatment pressure for OSA will also treat snoring.

The device can include a module/device that can administer any type of chemical (liquid/gas/solid particle) in aid of the patient. For example, aroma-therapy scents to calm a patient or a nebuliser that can administer an asthma drug if the device is used as a medical one.

A major advantage which will flow from the adoption of the method and apparatus of the present invention is that if the patient progresses to OSA (from snoring only), they may readily accept a mask system and positive airway pressure, albeit at higher pressures to the snoring device of the invention which they previously used, because they will be somewhat acclimatised to such a device being fitted to them. Non-compliance with prescribed CPAP treatment is a significant predictor of early death, and any method to improve compliance and reduce dropout rates would have significant impact on the community.

A further advantage of the invention is that it will facilitate the earlier identification of OSA, with a consequent improvement in life expectancy.

Other advantages to the patient include:

Effectively controls snoring therefore less sleep disturbance to bed partners and their families.

Controlling snoring may have a positive effect on marriages and relationships, particularly in view of a bed partner losing sleep during the night due to their partner snoring.

Indicates where some level or threshold has been reached and suggests to the patient when medical attention should be sought as their social problem (snoring) may have developed into a medical condition (OSA).

A non-invasive positive pressure airway system that can treat a patient from the onset of snoring that provides a technology path through to OSA. A system whereby the patient does not need to try many alternatives to have success. Positive airway pressure could provide a safe and efficacious treatment for the life of a patient. The patient does not need to pursue new technologies, does not need to relearn or acclimatise to vastly different forms of treatment. It may be argued that as we age, some are less comfortable to embrace change in our lives but view it as a threat.

The low positive airway pressure (PAP) and mask interface acclimatises the patient at an earlier stage of life, and therefore may accept CPAP interfaces and pressures in future should they require treatment for OSA. This may also encourage long-term compliance on CPAP and reduce dropout rates. One aspect of the invention relates the acclimatizing of the user for OSA treatment by supplying the user with pressures not sufficient to treat OSA, but high enough to treat snoring. This means more patients treated for longer. It should be noted in general that there are a greater number of user trade-offs to design masks and flow generators for the higher pressures required for CPAP, e.g. noise, size, and comfort.

Improved family life through less sleep disturbance to bed partner of other household members. Also identifying significant snoring or OSA at an earlier stage may have positive future outcomes for the patient, potentially extending life and/or improving health.

Potentially less side effects and low risk from positive airway pressure. For example oral appliances can result in teeth movement, jaw pain, bite changes.

It is desirable for the interface and head gear to be of a user friendly design with minimal obtrusiveness. It is preferable to be able to put on and to take off the interface and head gear from a patient's head, as easily as a hat or a cap.

If the device described above needs to incorporate electronics, there could be included flexible printed circuit boards. Such flexible printed circuit boards could be sewn or otherwise attached to the headgear or interface. The advantage of this is that better conformance to human anatomy can be achieved and this will also reduce the overall size and profile of the unit, helping to make it less obtrusive to the patient. The use of flexible printed circuit boards in this way will form, what is essentially, a wearable circuit.

The head gear (strap 22 shown in FIG. 1) or mask components can incorporate intelligent textiles that have the ability to transmit electrical signals to monitor the patient. For example skin temperature can be detected and monitored through the fibres. Such intelligent textiles will also assist to minimise the bulk of the device fitted to the patient's head.

Intelligent fibres can also be used to improve comfort to the patient. For example, the head gear could provide warming in winter or cooling in summer. The heating or cooling elements can be integrated into the system, otherwise intelligent textiles with phase change or conductive fibres may be used as heating and cooling elements or conduction elements.

It will be understood that the embodiments of the invention disclosed and defined herein extends to all alternative combinations of two or more of the individual features mentioned or evident from the text. All of these different combinations and even individual components or features constitute various alternative aspects of the invention.

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention. In addition, while the invention has particular application to patients who suffer from OSA, it is to be appreciated that patients who suffer from other illnesses (e.g., congestive heart failure, diabetes, morbid obesity, stroke, barriatric surgery, etc.) can derive benefit from the above teachings. Moreover, the above teachings have applicability for use with patients and non-patients alike, e.g., users of mask systems in general.

The invention claimed is:

1. A system for treatment of a user with a sleeping disorder, the system comprising:
    a flow generator not capable of supplying a maxinium gas pressure above about 8 cm $H_2O$, said maximum gas pressure or less being typically less than sufficient for treatment of obstructive sleep apnea (OSA), said flow generator being configured to deliver pressurized gas at the maximum gas pressure or less during an entire treatment session of a user;
    a user interface coupled to the flow generator and structured to deliver the pressurized gas to the use's airways;
    a monitor to generate a signal indicative of a sleeping pa,rameter of the user; and
    an alerting device configured to generate a visual or audible message,
    wherein said flow generator is configured to increase said gas pressure depending on the signal indicative of the sleeping parameter, and
    wherein if said gas pressure supplied by the flow generator is increased to equal to or greater than a predetermined pressure, the visual or audible message is provided to the user by the alerting device indicating the possible onset of OSA, without the intervention of a clinician.

2. The system according to claim 1, wherein the flow generator includes a motor that is directly mounted to the user interface.

3. The system according to claim I wherein the sleeping parameter is representative of the user's breathing cycle.

4. The system according to claim 3, wherein the sleeping parameter includes a snoring parameter of the user,
    and wherein the flow generator is configured to supply said pressurized gas if the snoring parameter is more than a predetermined amount.

5. The system according to claim 4, wherein the flow generator is configured to supply a minimum gas pressure to the user upon an initial indication that the snoring parameter is greater than said predetermined amount.

6. The system according to claim 5, wherein the flow generator is configured to increase a prevailing gas pressure until the monitored snoring parameter is less than said predetermined amount.

7. The system according to claim 6, wherein the flow generator is configured to increase the prevailing gas pressure continuously or stage-wise, if the monitored snoring parameter is greater than said predetermined amount.

8. The system according to claim 5, wherein if the flow generator supplies said pressurized gas to the user at a level that is greater than said minimum pressure, then the flow generator is configured to lower said gas pressure if the monitor indicates that the monitored snoring parameter is less than said predetermined amount.

9. The system according to claim 1, wherein the signal is representative of transitions between inspiration and expiration in the user's breathing cycle.

10. The system according to claim 9, wherein the flow generator is configured to deliver a magnitude of said pressurized gas during inspiration of the user that is higher than a magnitude of said pressurized gas supplied during expiration of the user.

11. The system according to claim 10, wherein a magnitude of pressurized gas supplied during inspiration of the user is 6 cm $H_2O$ or less.

12. The system according to claim 10, wherein an average magnitude of the pressurized gas supplied during inspiration is about 3-6 cm $H_2O$.

13. The system according to claim 10, wherein the magnitude of the pressurized gas supplied during exhalation of the user is negligible or nil.

14. The system according to claim 9, wherein the flow generator is configured to supply a pulse of pressurized gas during inspiration of the user.

15. The system according to claim 1, wherein the flow generator is configured to deliver a substantially constant magnitude of said pressurized gas during the entire breathing cycle of the user.

16. The system according to claim 1, further comprising a memory configured to record a magnitude of pressurized gas provided to the user,
wherein the alerting device is configured to generate the visual or audible message if said memory indicates that the user has received said predetermined pressure or higher for more than a predetermined number of treatment sessions.

17. The system according to claim 16, wherein said predetermined number of treatment sessions is two or more.

18. The system according to claim 1, wherein the predetermined pressure is greater than about 6 cm $H_2O$.

19. The system according to claim 1, further comprising a bacterial filter or filtration system configured to filter pressurized gas before being applied to the user.

20. The system according to claim 1, further comprising a valve provided to the user interface, the valve being open during expiration of the user.

21. The system according to claim 1, further comprising a controller configured to operate the flow generator.

22. The system according to claim 21, wherein the controller includes a flexible member built into a headgear that is configured to support the user interface on the user.

23. The system according to claim 22, wherein the headgear comprises a textile, having phase change fibers and/or conductive fibers.

24. The system according to claim 1, wherein the maximum pressure is less than 8 cm $H_2O$.

25. A non-invasive method of predicting the possible onset of obstructive sleep apnea (OSA) using a flow generator system, the flow generator system including a flow generator and an alerting device, the method comprising:
monitoring a snore parameter of a user with a monitor;
generating a signal indicative of the snore parameter with the monitor;
applying gas under positive pressure to the user's airways with the flow generator in dependence on the signal indicative of the snore parameter, said positive pressure being typically insufficient for treatment of OSA; and
generating a visual or audible message via the alerting device of the flow generator system, and without intervention of a clinician, if the positive pressure gas is greater than a predetermined maximum pressure,
wherein the visual or audible message indicates the possible need to diagnose or treat the user for OSA and the visual or audible message recommends that, the user consult a physician regarding the possible onset of obstructive sleep apnea.

26. The method according to claim 25, wherein pressurized gas is not supplied to the user if the monitored snore parameter is less than a predetermined amount.

27. The method according to claim 25, wherein, if the monitored parameter is greater than a predetermined amount, applying the gas under positive pressure to the user's airways.

28. The method according to claim 27, wherein the application of pressurized gas is manually controlled by the user and/or a bed partner.

29. The method according to claim 27, wherein the snore parameter is based on sound and/or pressure.

30. The method according to claim 25, wherein the maximum. pressure is more than 6 cm $H^2O$.

31. The method according to claim 30, wherein the predetermined maximum pressure is equal to or less than 6 cm $H_2O$, such that there is no indication that OSA may be present.

32. The method according to claim 31, further comprising indicating that no OSA is present.

33. The method according to claim 25, wherein the flow generator system includes a product manual, and
wherein generating the visual or audible message further comprises instructing the user to consult the product manual.

34. A non-invasive method of treating snoring of a snorer, the method comprising:
using a flow generator not capable of generating a flow of gas pressurized above a maximum pressure of about 8 cm $H_2O$, said maximum pressure or less being typically less than sufficient for treatment of obstructive sleep apnea (OSA);
measuring a snoring parameter with a monitor;
applying positive airway pressure to the snorer's airways with the flow generator in use up to the maximum pressure or less during an entire respiratory cycle of the snorer, for each of a plurality of treatment sessions of the snorer, said positive airway pressure depending on the snoring parameter measured by the monitor; and
generating a visual or audible message with an alerting device indicating the likely onset of OSA if said positive airway pressure exceeds a predetermined threshold,
wherein said snorer has not been diagnosed with OSA.

35. The method according to claim 34, wherein the maximum pressure is about 6 cm $H_2O$ or less.

36. The method according to claim 34, wherein an average pressure range applied to the snorer during a treatment session is between about 3-6 cm.

37. A modular system for treatment of a user with a progressively worsening sleeping disorder, the system comprising:
a snore-only treatment module configured for treatment of snoring of the user, the snore-only treatment module including a first flow generator not being capable of generating a flow of gas pressurized above a maximum pressure of about 8 cm $H_2O$, said maximum gas pressure or less being, typically less than sufficient for treatment of obstructive sleep apnea (OSA);
an OSA/snore treatment module configured for treatment of OSA and snoring of the user, said OSA: snore treatment module comprising only a second flow generator configured to generate gas pressurized in the range of 4-20 cm $H_2O$;
an upgradable base unit configured to be directly and removably coupled with the snore-only treatment module or the OSA/snore treatment module such that in use only one of the snore-only treatment module and the OSA/snore treatment module is operable to provide treatment;
a monitor to generate a signal indicative of a sleeping parameter of the user; and
an alerting device configured to generate a visual or audible message,
wherein said first flow generator is configured to increase said gas pressure depending on the signal indicative of the sleeping parameter, and wherein if said gas pressure supplied by the first flow generator is increased to equal to or greater than a predetermined pressure, the visual or audible message is provided to the user by the alerting device indicating the possible onset of OSA and that the user should attach the OSA/snore treatment module to the upgradable base unit, without the intervention of a clinician.

38. The system according to claim 37, wherein the upgradable base unit includes a user interface.

39. The system according to claim 38, wherein the user interface is configured to directly mount a motor of the snore-only treatment module, and is configured to cooperate with a gas delivery conduit that is in communication with the OSA/snore treatment module.

40. A system of managing a snorer, the system comprising:
   means for supplying positive airway pressure, said means for supplying not being capable of supplying a maximum pressure above about 8 cm $H_2O$;
   means for determining according to predetermined criteria the likely onset of OSA;
   means for measuring a snoring parameter; and
   means for providing an audible or visual alert to the snorer, wherein said means for supplying positive airway pressure is configured to generate pressurized gas suitable for treatment of snoring, but typically less than sufficient for treatment of OSA, depending on the snoring parameter during an entire treatment session of the snorer, and
   wherein if said means for supplying positive airway pressure supplies positive pressure equal to or greater than a predetermined threshold, then said means for providing the audible or visual alert is configured to provide the audible or visual alert stating the possible onset of OSA without intervention of a clinician.

41. The system according to claim 40, wherein said means for applying positive airway pressure is configured to deliver pressurized gas in an average pressure range of 8 cm $H_2O$ or less during an entire respiratory cycle of the snorer.

42. The system according to claim 41, wherein the average pressure range is about 3-6cm $H_2O$.

43. A non-invasive method for acclimatizing a user for potential future treatment of obstructive sleep apnea (OSA) using a flow generator not capable of supplying a flow of gas above a maximum pressure of about 8 cm $H_2O$, said maximum gas pressure or less being typically less than sufficient for treatment of OSA, the method comprising:
   providing the user with a patient interface;
   measuring a sleeping parameter of the user with a monitor;
   applying gas to the patient interface at or below the maximum pressure depending on the sleeping parameter during the entirety of each of a plurality of treatment sessions such that the user becomes acclimatized to the treatment of OSA provided by the flow of gas; and
   generating a visual or audible message to the user with an alerting device stating the likely onset of OSA,
   wherein said method is conducted prior to the diagnosis of OSA in said user.

44. A non-invasive method of managing a snorer, the method including:
   treating snoring using a positive airway pressure apparatus with pressurized gas at a pressure less than typically sufficient for treatment of obstructive sleep apnea (OSA) during a period in the life of the snorer when the snorer has not been diagnosed with OSA, measuring a snoring parameter with a monitor, said pressure being dependent on said snoring parameter, treating snoring further including determining according to predetermined criteria the likely onset of OSA, and alerting the snorer with a visual or audible message generated by an alerting device stating the possible onset of OSA without the intervention of a clinician when a monitor detects that the positive pressure apparatus is supplying gas pressure at a pressure above a predetermined threshold.

45. The method according to claim 44, further comprising substituting continuous positive air pressure treatment (CPAP) for anti-snoring treatment at the onset of OSA.

46. A method for indicating to a patient treated for snoring the likely onset of obstructive sleep apnea (OSA), the method comprising:
   applying a first positive pressure to the patient's airways with a flow generator;
   monitoring a snoring parameter of the patient with a monitor;
   comparing the snoring parameter with a first predetermined value with a controller;
   if the controller determines that the snoring parameter is higher than the first predetermined value, instructing the flow generator with the controller to automatically increase the first positive pressure to a second positive pressure;
   comparing the second positive pressure with a second predetermined value with the controller; and
   if the controller determines that the second positive pressure is higher than the second predetermined value, indicating to the patient via an alerting device with a visual or audible message that states the likely onset of OSA without the intervention of a clinician,
   wherein the first and the second positive pressures are typically insufficient for treating OSA.

47. The method of claim 46, wherein the method is applied in a plurality of snoring treatment sessions and the likely onset of OSA is indicated to the patient only if the second positive pressure exceeds the second predetermined value during more than a predetermined number of treatment sessions.

48. The method of claim 46, wherein the first and the second positive pressures are below 8 cm $H_2O$.

49. The method of claim 46, wherein the first positive pressure is zero.

50. The method of claim 46, wherein monitoring the snoring parameter comprises detecting pressure fluctuations characteristic of snoring.

51. The method of claim 46, wherein the first and the second positive pressures are less than 8 cm $H_2O$.

52. A respirator system for indicating to a patient treated for snoring the likely onset of obstructive sleep apnea (OSA), the system comprising:
   an airflow generator and an air mask system configured to apply gas at a first positive pressure to the patient's airways;
   a detector configured to detect a snoring parameter of the patient;
   an device configured to generate a visual or audible signal based on the snoring parameter detected by the detector, the device including an indicator; and
   a controller configured to:
      monitor the snoring parameter of the patient;
      compare the snoring parameter with a first predetermined value;
      if the snoring parameter is higher than the first predetermined value, send a signal to the airflow generator to increase the first positive pressure to a second positive pressure;
      compare the second positive pressure with a second predetermined value; and if the second positive pressure is higher than the second predetermined value, provide a message to the patient, via the device and the indicator, indicating the likely onset of OSA without the intervention of a clinician, wherein the first and the second positive pressures are typically insufficient for treating OSA.

53. The respirator system of claim 52, the system further comprising memory configured to store data associated with the snoring parameter or the applied positive pressure during one or more snoring treatment sessions.

* * * * *